United States Patent
Porter

(10) Patent No.: US 11,400,214 B2
(45) Date of Patent: Aug. 2, 2022

(54) INJECTION FLUID QUANTIFICATION

(71) Applicant: ACIST Medical Systems, Inc., Eden Prairie, MN (US)

(72) Inventor: Blaise D. Porter, Minneapolis, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 188 days.

(21) Appl. No.: 16/706,245

(22) Filed: Dec. 6, 2019

(65) Prior Publication Data

US 2021/0170099 A1    Jun. 10, 2021

(51) Int. Cl.
| | |
|---|---|
| *A61M 5/172* | (2006.01) |
| *A61M 5/168* | (2006.01) |
| *A61M 25/01* | (2006.01) |
| *A61M 5/00* | (2006.01) |
| *A61M 25/00* | (2006.01) |

(52) U.S. Cl.
CPC .......... *A61M 5/1723* (2013.01); *A61M 5/007* (2013.01); *A61M 5/1684* (2013.01); *A61M 25/0084* (2013.01); *A61M 25/01* (2013.01); *A61M 2025/0002* (2013.01); *A61M 2205/3331* (2013.01)

(58) Field of Classification Search
CPC .............. A61M 5/168; A61M 5/16831; A61M 5/16836; A61M 5/16854; A61M 5/16859; A61M 5/172; A61M 5/1723; A61M 2005/1726; A61M 2025/0001; A61M 2025/0002; A61M 2205/3331; A61M 2205/3344; A61M 5/007
See application file for complete search history.

(56) References Cited

U.S. PATENT DOCUMENTS

| | | |
|---|---|---|
| 5,807,321 A | 9/1998 | Stoker et al. |
| 2007/0106218 A1* | 5/2007 | Yodfat ................. A61M 5/1413 604/131 |
| 2014/0024954 A1* | 1/2014 | Frinak ................. A61M 1/3655 600/485 |
| 2015/0119709 A1 | 4/2015 | Coolidge et al. |
| (Continued) | | |

OTHER PUBLICATIONS

PCT International Search Report and Written Opinion dated Aug. 28, 2020 for related International Application No. PCT/US2019/065034, 11 pgs.

*Primary Examiner* — Kami A Bosworth
(74) *Attorney, Agent, or Firm* — Fredriksen & Byron, P.A.

(57) ABSTRACT

Methods and systems may quantify how much contrast fluid is injected into a patient by a powered fluid injector. A controller of the powered fluid injector can receive a command from a user to begin dispensing contrast fluid. The controller may determine whether a hemodynamic pressure signal is present from a pressure sensor in fluidic connection with the vasculature of the patient. The powered fluid injector may dispense a quantity of contrast fluid in response to the command. The controller may add the quantity of contrast fluid to an injection quantity if the hemodynamic pressure signal is present just prior to and/or just after the quantity of contrast fluid is dispensed. The controller may refrain from adding the quantity of contrast fluid to the injection quantity if the hemodynamic pressure signal is not present just prior to and/or just after the quantity of contrast fluid is dispensed.

10 Claims, 6 Drawing Sheets

(56) References Cited

U.S. PATENT DOCUMENTS

| | | | |
|---|---|---|---|
| 2015/0246173 A1* | 9/2015 | Steger | A61M 1/3656 604/6.01 |
| 2018/0020935 A1* | 1/2018 | Eagle | A61B 5/7235 600/487 |
| 2020/0324038 A1* | 10/2020 | Bloomberg | A61M 1/1601 |

* cited by examiner

INJECTION FLUID QUANTIFICATION

TECHNICAL FIELD

This application relates generally to the field of medical injection technology and, more particularly, to devices and methods for quantifying the amount of fluid that has been injected into a patient.

BACKGROUND

Many medical imaging procedures, such as angiography, involve injecting a contrast fluid into a patient. Angiography is a procedure used in the diagnosis and treatment of cardiovascular conditions, including abnormalities or restrictions in blood vessels. During angiography, a radiographic image of the heart or vascular structure is obtained by injecting contrast fluid through a catheter into the vasculature (e.g., the coronary artery) of the patient. The injected contrast fluid can pass to vascular structures in fluid communication with the blood vessel in which the injection is made. X-rays are passed through the region of the body in which the contrast fluid was injected. The X-rays are absorbed by the contrast fluid, causing a radiographic outline or image of the vasculature containing the contrast fluid. Contrast injection can be used in conjunction with other medical procedures as well, such as optical coherence tomography (OCT) imaging, intravascular ultrasound (IVUS) imaging, computed tomography (CT) imaging, magnetic resonance imaging (MRI), and interventional device procedures/placements.

A powered fluid injector can be utilized to inject amounts of the contrast fluid into the patient during such medical procedures. However, conventional powered fluid injectors are unable to quantify how much contrast fluid is actually injected into the patient. For instance, contrast fluid may be dispensed from the powered fluid injector for a variety of reasons (e.g., to purge fluid lines, to perform a wet connect of system components, to prime the powered fluid injector for use) without ever entering the patient's vasculature. Thus, a user (e.g., a physician) using a conventional powered fluid injector is left to approximate the amount of contrast fluid injected into the patient.

SUMMARY

Embodiments disclosed herein quantify how much fluid that is dispensed from a powered fluid injector is actually injected into a patient rather than used for other non-injection purposes. Some embodiments determine whether dispensed fluid was injected or not based on whether an invasive blood pressure sensor detects a hemodynamic pressure signal (injected) or not (not injected) in temporal proximity to when the fluid was dispensed. A quantity of dispensed fluid that is determined to have been injected into a patient is added to an injection quantity, while a quantity of dispensed fluid that is determined not to have been injected into a patient is not added to the injection quantity. Calculating the injection quantity in this manner provides an objective measurement of how much of the dispensed fluid was injected into the patient as opposed to being used for other purposes. Such an objective measurement is superior to a user estimating how much dispensed fluid was used for non-injection purposes.

DETAILED DESCRIPTION

The following detailed description is exemplary in nature and provides some practical illustrations and examples. Those skilled in the art will recognize that many of the noted examples have a variety of suitable alternatives.

A number of various exemplary flow measurement techniques are disclosed herein using the description provided as follows in addition to the accompanying drawings. Each of the techniques disclosed herein can, in some examples, be employed independently or in combination with one or more (e.g., all) of the other techniques disclosed herein.

Figure 1:
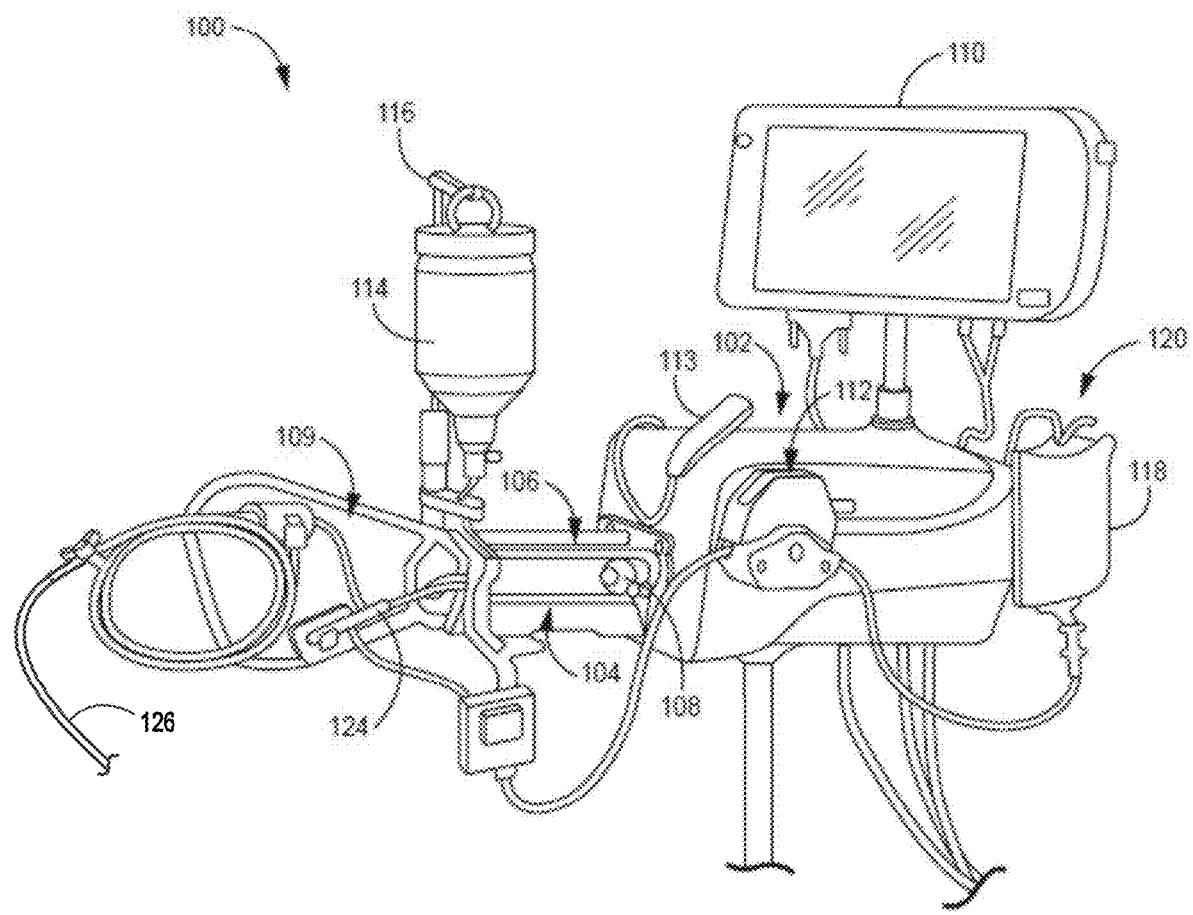
FIG. 1 is a perspective view of an embodiment of a powered fluid injector.

FIG. 1 illustrates a perspective view of an exemplary embodiment of a powered fluid injector 100. In operation, the powered fluid injector 100 can inject a quantity of fluid into a patient, for instance into a vessel of a patient via a catheter. The fluid injected by the powered fluid injector 100 can be, for example, a contrast fluid, a non-contrast fluid (e.g., saline), or a combination thereof. By injecting a quantity of fluid into a patient, the powered fluid injector 100 can facilitate a variety of medical diagnostic and/or interventional procedures, including the collection of image data representing an anatomical region of interest. These procedures can include, as examples, optical coherence tomography (OCT) imaging, intravascular ultrasound (IVUS) imaging, computed tomography (CT) imaging, magnetic resonance imaging (MM), angiographic procedures, and interventional device procedures/placements.

The illustrated powered fluid injector 100 includes a drive assembly housing 102 and a sleeve 104. The sleeve 104 can be secured to the drive assembly housing 102. For example, the drive assembly housing 102 can include an opening, and the sleeve 104 can be secured to the drive assembly housing 102 at or near such opening. The sleeve 104 may extend out from the drive assembly housing 102 and may be configured to receive and hold a reservoir 106. The reservoir 106 can have an internal reservoir volume containing a fluid and can include a plunger 108 within the internal reservoir volume. At least a portion of a drive assembly can be housed within the drive assembly housing 102.

The drive assembly can be configured to pressurize fluid within the internal reservoir volume. For instance, the drive assembly may couple to the plunger 108, such as at the opening in the drive assembly housing 102, and drive the plunger 108 within the internal reservoir volume. As the plunger 108 is progressively driven within the reservoir 106, fluid within the internal reservoir volume can be output from the reservoir 106 along tubing 109 leading to a catheter 126 that is inserted into a patient's blood vessel to inject the fluid into the vasculature. In certain applications of the powered fluid injector 100, output fluid, such as contrast media, can be pressurized anywhere from 1000-1500 psi (e.g., 1200 psi).

The illustrated embodiment of the powered fluid injector 100 includes several features that can be useful in pressurizing and delivering fluid during operation. The powered fluid injector 100 can include a controller 110. The controller 110 can include a user interface for various operational aspects. For example, the controller 110 can be utilized by a user to set up various parameters and/or protocols to be used for a given fluid injection procedure. In one example, the user can interact with the controller 110 to input fluid injection parameters such as flow rate, injection volume (e.g., maximum), injection pressure limit (e.g., maximum), fluid injection duration, rise time, and/or other injection parameters. In one embodiment, the controller 110 includes a touch-screen panel display, enabling a user to view and modify injection parameters. The controller 110 can also be used to initialize the powered fluid injector 100 (e.g., to prepare it for a patient fluid injection), or to activate certain features or sequences of operation. The controller 110 may also provide status information, including information related to past or currently ongoing injection procedures as well as any appropriate alerts. The controller 110 can include an imaging engine having one or more processors for controlling operation of the powered fluid injector 100. Such processors can also control other components, such as the drive assembly, a peristaltic pump 112, when present, and/or any sensors and detectors included at the powered fluid injector 100.

In addition to the controller 110, the illustrated powered fluid injector 100 includes a hand-control device 113 for user input. The hand-control device 113 can be coupled to the controller 110 either wirelessly or via a lined connection. Although in other embodiments, the hand-control device 113 can be connected to a component of the powered fluid injector 100 other than the controller 110, such as drive assembly housing 102. The hand-control device 113 can generate and send various signals related to an injection procedure to the controller 110 or other connected component. A user can actuate one or more interface components at the hand-control device 113 to control an injection procedure. For example, the user can use hand-control device 113 as a variable-rate control device to alter the fluid flow rate output from the powered fluid injector 100 and/or as a mechanism for starting or stopping a fluid injection.

The powered fluid injector 100 can also include one or more components useful for supplying fluid to be used in an injection procedure. A container 114 can include a supply of fluid, such as contrast media, and be secured to a holder 116 at the powered fluid injector 100. Fluid from the container 114 can be supplied to the reservoir 106 for use during an injection procedure. For example, fluid from the container 114 can be drawn into the reservoir 106 when the plunger 108 is being retracted (e.g., moved in a direction toward the drive assembly housing 102) and thereby refill the internal reservoir volume. Similarly, when the powered fluid injector 100 includes the peristaltic pump 112, a second container 118 can include a supply of fluid, such as a flushing medium (e.g., saline), and be secured to a holder 120 at the powered fluid injector 100. When present, the peristaltic pump 112 can receive fluid from the second container 118 and deliver such fluid to the patient. Often times, the peristaltic pump 112 may be used to deliver non-contrast fluid, such as saline, at a lower pressure than that at which the drive assembly delivers contrast fluid from the reservoir 106. A valving system 124 can be included to selectively place the reservoir 106 or peristaltic pump 112 in communication with the patient.

As described elsewhere herein, the controller 110 of the powered fluid injector 100 may control various functions of the powered fluid injector 100, which may include dispensing contrast fluid out through tubing. In some embodiments, the controller 110 may be housed in a housing of a display device. In some embodiments, the controller may be housed in the injector housing.

The powered fluid injector may be connected to a catheter 126, fluidly and electrically, that is inserted into a blood vessel (e.g., the coronary artery) of a patient. When so connected, the powered fluid injector can inject contrast fluid or dispense non-contrast fluid into the patient's vasculature via the injector tubing and the catheter 126. In many embodiments, the catheter 126 may include an invasive blood pressure sensor. The blood pressure sensor may be in electrical communication with the controller when the powered fluid injector is connected to the catheter 126. The blood pressure sensor may provide a blood pressure signal to the controller when the catheter 126 is in fluidic connection with the powered fluid injector and may not provide a blood pressure signal when the catheter 126 is not in fluidic connection with the powered fluid injector.

Figure 2A:
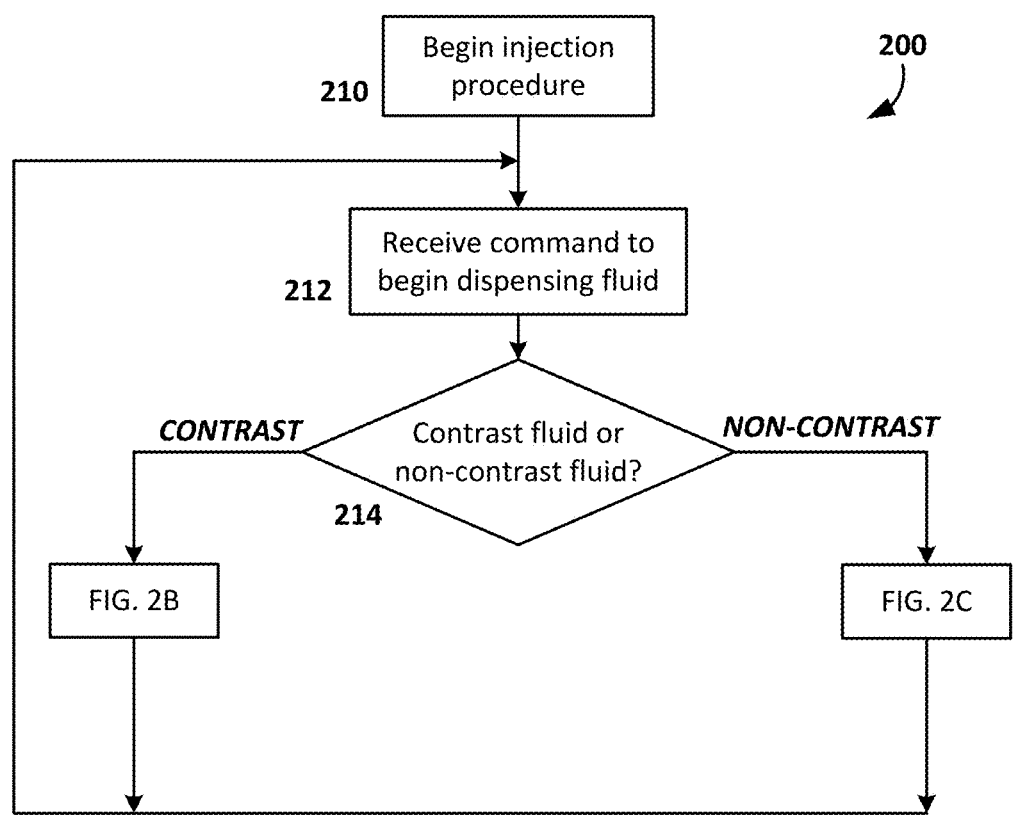
FIG. 2A is a flowchart of an illustrative method for dispensing a contrast fluid and/or a non-contrast fluid as part of an injection procedure.
Figure 2B:
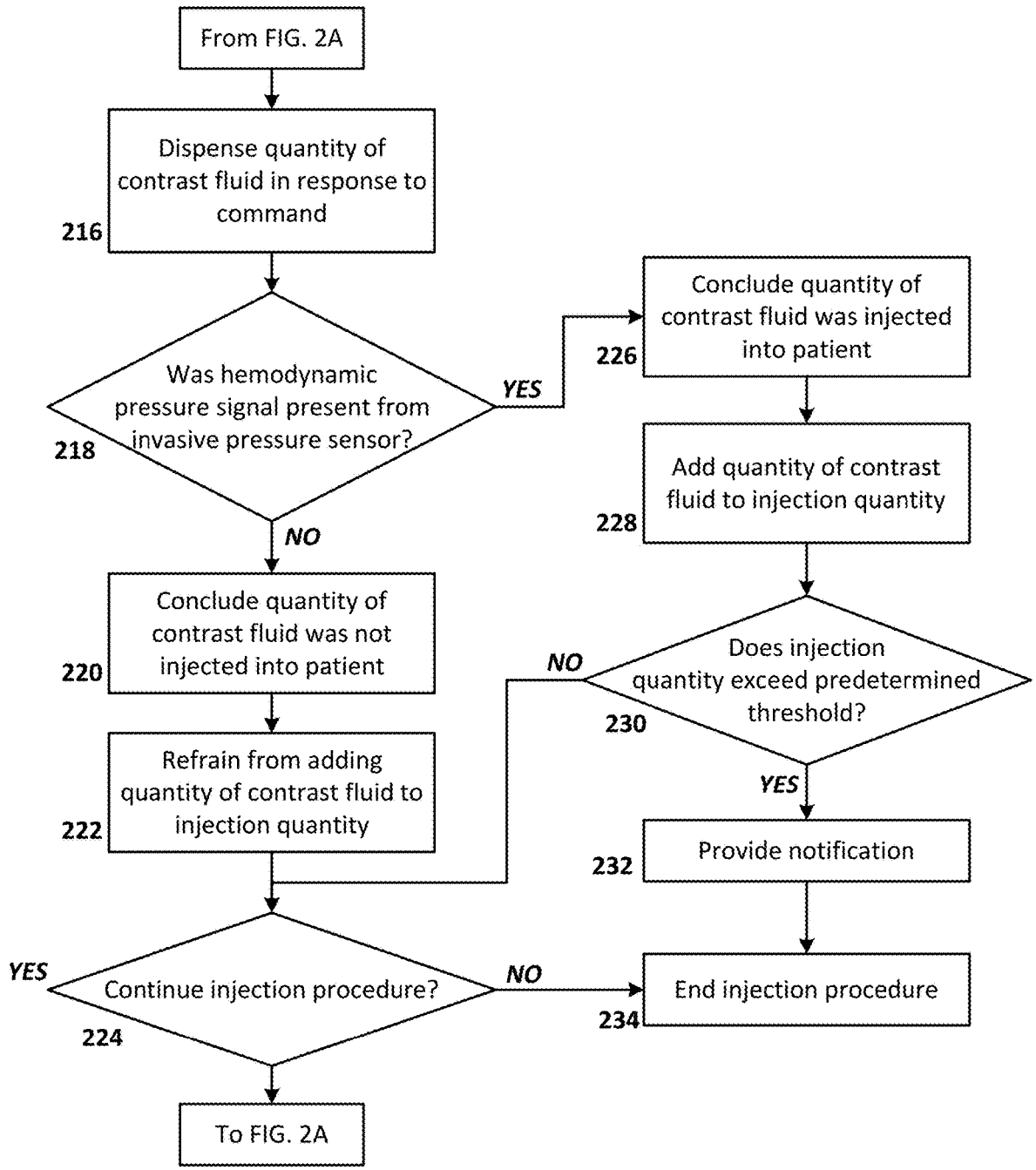
FIG. 2B is a flowchart of an illustrative method for quantifying how much contrast fluid dispensed by a powered fluid injector is injected into a patient vs. not injected into the patient.
Figure 2C:
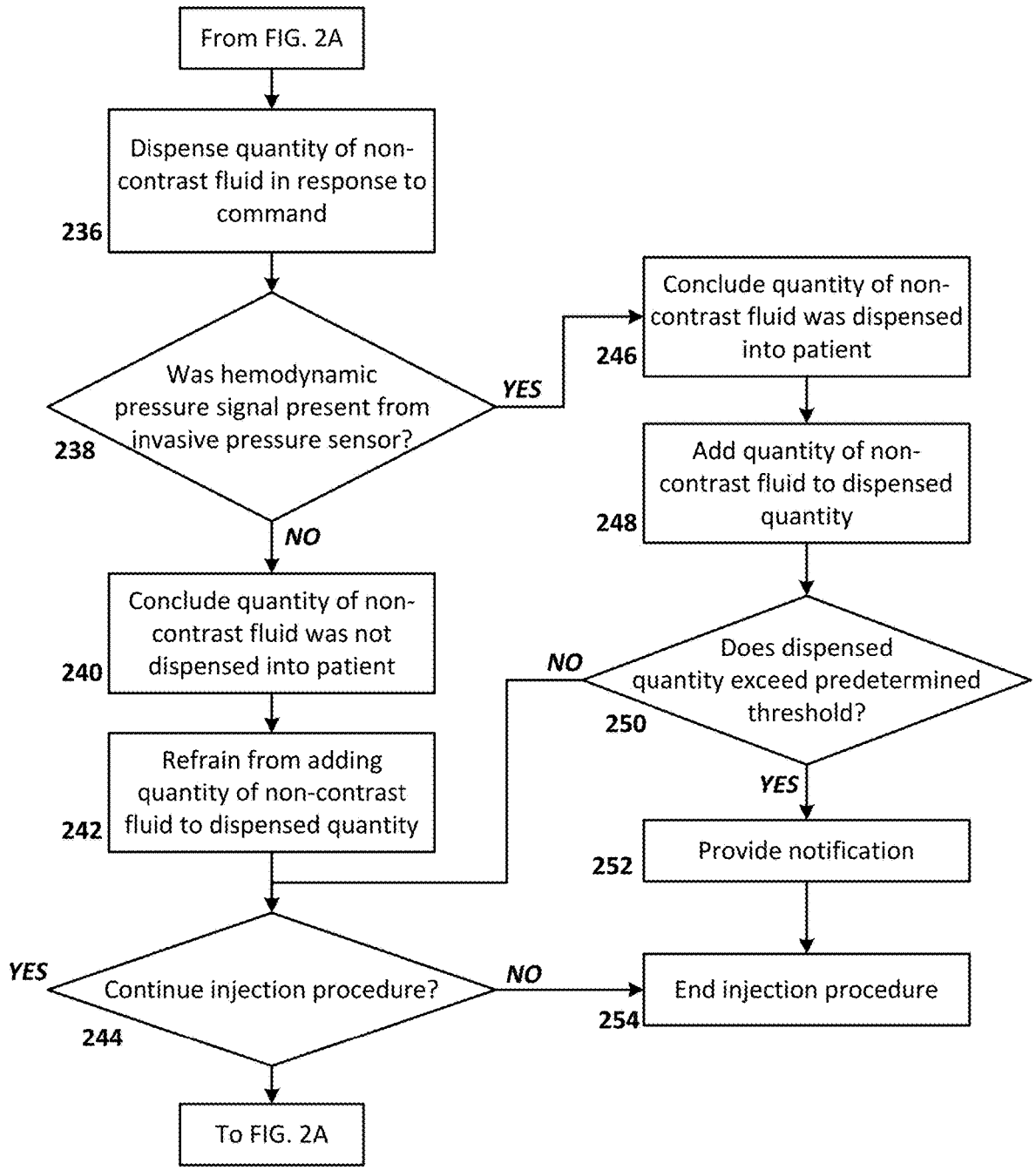
FIG. 2C is a flowchart of an illustrative method for quantifying how much non-contrast fluid dispensed by a powered fluid injector is dispensed into a patient vs. not dispensed into the patient.

FIGS. 2A-2C illustrate a method 200 for quantifying the amount of fluid (contrast fluid and/or non-contrast fluid) that has been injected, via the powered fluid injector, into a patient during an injection procedure. An injection procedure may begin 210 with such steps as preparing the injection equipment and making sure the patient is fully prepared. In many instances, an injection procedure is one of multiple procedures being performed on a patient as part of a medical intervention. The catheter that is inserted into the patient's blood vessel may be accessed by equipment other than the powered fluid injector for performing various other procedures on the patient. In some instances (e.g., in a cardiac catheterization lab), there may be multiple injection procedures interspersed among other procedures in a medical intervention.

At various instances, contrast fluid may be dispensed from the powered fluid injector that is not injected into the patient. For example, the powered fluid injector may dispense contrast fluid into a waste receptacle or onto a surgical table (not into a patient's blood vessel) when purging all air bubbles from the system. Such purging may occur any time air must be removed from the line (e.g., cavitation, bad connection, initial setup, changing catheters (e.g., diagnostic to interventional), adding microcatheters for an intervention, etc.). In some instances, users may flush first with saline and then with contrast fluid. In another example, a user may dispense contrast fluid to drive saline out of the injector tubing (e.g., if the tubing was filled with saline to improve the hemodynamic pressure signal). In another example, a user may cause the powered fluid injector to dispense a small amount of contrast fluid to facilitate a wet connection between two components of an injection system (e.g., injector tubing to the catheter that is inserted into the patient's blood vessel, stopcock to pressure line, stopcock to catheter, etc.). In another example, a user may otherwise test the system (e.g., for leaks) by dispensing contrast fluid into a waste receptacle or onto a surgical table (not into a patient's blood vessel). For similar purposes, non-contrast fluid may be dispensed from the powered fluid injector not into a patient's vasculature.

The controller may receive a command from a user (e.g., a cardiologist) to begin dispensing fluid 212 for an injection procedure (e.g., a medical imaging procedure). The user may provide the command to the controller via a hand controller, via a touchscreen, or via another suitable input device. In some instances, the command may be automated through the injector. The controller may determine whether the user's command was to begin dispensing contrast fluid or non-contrast fluid 214. FIG. 2B illustrates one embodiment of what the controller may do if the command was to begin dispensing contrast fluid. FIG. 2C illustrates one embodiment of what the controller may do if the command was to begin dispensing non-contrast fluid.

The controller may determine how much of the fluid that was dispensed was actually delivered through a catheter into the patient's blood vessel. The controller may measure the quantity of fluid that was delivered into the patient's vasculature rather than relying on a user's estimate of how much of the total dispensed fluid was not delivered into the patient's vasculature.

To determine whether a specific quantity of fluid is delivered into a patient's vasculature or not, the controller may determine whether a hemodynamic pressure signal is present from an invasive pressure sensor in fluidic connection with the patient's vasculature. As noted, in some embodiments, the pressure sensor may be in fluidic connection with the catheter that is positioned within the patient's vasculature. In some embodiments, the catheter may be a guide catheter. In some embodiments, the catheter may be a diagnostic catheter.

The pressure sensor may be configured to provide a hemodynamic pressure signal to the controller only when the catheter is connected to and brought into fluidic connection with the powered fluid injector's tubing. The pressure sensor is in electrical communication with the controller. When the preliminary steps of the injection procedure have been completed and the user is ready to deliver a quantity of fluid into the patient's vasculature, the catheter that is positioned within the patient's vasculature may be connected to and brought into fluidic connection with tubing of the powered fluid injector. Before such connection, the pressure sensor may not provide a hemodynamic pressure signal to the controller. After such connection, with the pressure sensor in fluidic connection with the patient's vasculature and in electrical communication with the controller, the pressure sensor may detect the patient's blood pressure and provide a hemodynamic pressure signal to the controller. If the catheter is disconnected from the powered fluid injector again, the pressure sensor may not provide a hemodynamic pressure signal because the pressure sensor is no longer in fluidic connection with the catheter.

In some instances, the controller may determine whether the hemodynamic pressure signal is present in close time proximity to when the powered fluid injector begins dispensing fluid. For example, the controller may be configured to determine whether the hemodynamic pressure signal is present before causing the powered fluid injector to begin dispensing the quantity of fluid. In such examples, the controller may receive the command from the user to begin dispensing fluid and determine if the hemodynamic pressure signal is present before causing the powered fluid injector to begin dispensing a quantity of fluid. According to some examples, the controller may be configured to determine whether the hemodynamic pressure signal is present after causing the powered fluid injector to cease dispensing the quantity of fluid. In such examples, the controller may receive the command from the user to cease dispensing fluid and cause the powered fluid injector to cease dispensing a quantity of fluid before determining if the hemodynamic pressure signal is present.

In some embodiments, the controller may determine whether the hemodynamic pressure signal is present within a predetermined amount of time of when the powered fluid injector begins dispensing fluid. The controller may be configured to determine whether the hemodynamic pressure signal is present within a predetermined amount of time (e.g., 20-30 milliseconds) of causing the powered fluid injector to dispense the quantity of fluid. In some instances, the controller may be configured to determine whether the hemodynamic pressure signal is present within a predetermined amount of time before the controller causes the powered fluid injector to begin dispensing the quantity of fluid. In some instances, the controller may be configured to determine whether a hemodynamic pressure signal is present within a predetermined amount of time of the powered fluid injector completing dispensing of the quantity of fluid.

In some embodiments, the controller may determine whether a hemodynamic pressure signal is present multiple times during an injection procedure. In various instances, the controller may be configured to determine whether a hemodynamic pressure signal is present within a first predetermined amount of time before the controller causes the powered fluid injector to begin dispensing the quantity of fluid and within a second predetermined amount of time of the controller causing the powered fluid injector to cease dispensing the quantity of fluid. In some instances, the controller may be configured to determine whether a hemodynamic pressure signal is present within a predetermined amount of time of the powered fluid injector completing dispensing of the quantity of fluid. Making such determinations multiple times may confirm to the user and/or controller that the catheter is actually connected to the powered fluid injector and as such, may inhibit inaccurately tabulating the injection quantity. This feature may be especially helpful in injection procedures that require dispensing fluid at multiple times. For instance, if there is a hemodynamic pressure signal present before and after dispensing the quantity of fluid, the controller may conclude that the fluid was delivered into the patient. If there is a hemodynamic pressure signal present before but not after or after but not before dispensing the quantity of fluid, the controller may not conclude that the contrast fluid was delivered into the patient.

Referring to FIG. 2B, the controller may cause the powered fluid injector to dispense a quantity of contrast fluid in response to the user command 216. The controller may be configured to determine whether a hemodynamic pressure signal is present from the blood pressure sensor 218. The controller may determine an injection quantity of contrast fluid that is actually injected into the patient based on whether a hemodynamic pressure signal is present in conjunction with the dispensation of contrast fluid. The controller may assess any pressure signal received from the pressure sensor to determine if it has one or more attributes consistent with those of a valid hemodynamic pressure signal (e.g., a specific amplitude, a specific periodicity, etc.). The controller may be configured to refrain from adding a quantity of dispensed contrast fluid to an injection quantity if no hemodynamic pressure signal is present in temporal proximity to when the quantity of contrast fluid is dispensed. When no hemodynamic pressure signal is present in such instances, the controller may conclude that the quantity of contrast fluid was not injected into the patient 220 and may refrain from adding the quantity of contrast fluid to the injection quantity 222. The controller may be configured to add the quantity of dispensed contrast fluid to an injection quantity if a hemodynamic pressure signal is present in temporal proximity to when the quantity of contrast fluid is dispensed. When the hemodynamic pressure signal is present in such instances, the controller may conclude that the quantity of contrast fluid was injected into the patient 226 and may continue by adding the quantity of contrast fluid to the injection quantity 228. Thus, by adding or refraining from adding the quantity of dispensed contrast fluid to the injection quantity based on the presence of a hemodynamic pressure signal, the injection quantity may accurately reflect how much contrast fluid was actually injected into the patient.

As noted, in some examples, the controller may assess any pressure signal received from the pressure sensor to determine if the pressure signal constitutes a valid hemodynamic pressure signal. The controller may assess the amplitude of the pressure signal (e.g., compare the amplitude with that of a typical hemodynamic pressure signal). The controller may assess the periodicity of the pressure signal (e.g., compare the periodicity with that of a typical hemodynamic pressure signal). In some examples, the controller may assess both the amplitude and the periodicity of the pressure signal.

The controller may be able to compare the injection quantity to a predetermined threshold to protect against injecting too much contrast fluid into a patient. As shown, the controller may determine whether the injection quantity exceeds a predetermined threshold 230. The predetermined threshold may be based on complications associated with harmful amounts of the type of contrast fluid used in the injection procedure. Such complications may include Contrast Induced Nephropathy (CIN), associated with injecting too much contrast fluid into a patient. In some embodiments, the controller may be configured to notify the user (e.g., via the user interface) if the injection quantity exceeds the predetermined threshold. When the injection quantity exceeds the predetermined threshold, the controller may provide a notification 232. In some instances, when a notification occurs, the injection procedure may end 234. In some instances, there may be multiple notifications depending on how close the injection quantity is getting to a level that might cause harm to a patient. In some embodiments, a user may progressively inject quantities of contrast fluid into the patient's vasculature during an injection procedure and be notified before injecting undesired quantities of contrast fluid into the patient.

As shown, at different points during the injection procedure, the user can determine whether or not to continue the injection procedure 224. To continue the injection procedure, the user may again provide a command to begin dispensing fluid to the controller (212 of FIG. 2A), and the procedure can continue as described. To discontinue the injection procedure, for example, after imaging is complete, the user may end the injection procedure 234 and not inject any more quantities of contrast fluid into the patient. When the injection procedure has ended 234, a final injection quantity, corresponding to the total quantity of contrast fluid that was actually injected into the patient, can be provided to the user and subsequently to the patient's medical record.

Referring to FIG. 2C, the controller may cause the powered fluid injector to dispense a quantity of non-contrast fluid in response to the user command 236. The controller may be configured to determine whether a hemodynamic pressure signal is present from the blood pressure sensor 238. The controller may determine a dispensed quantity of non-contrast fluid that is actually dispensed into the patient based on whether a hemodynamic pressure signal is present in conjunction with the dispensation of non-contrast fluid. The controller may assess any pressure signal received from the pressure sensor to determine if it has one or more attributes consistent with those of a valid hemodynamic pressure signal (e.g., a specific amplitude, a specific periodicity, etc.). The controller may be configured to refrain from adding a quantity of dispensed non-contrast fluid to a dispensed quantity if no hemodynamic pressure signal is present in temporal proximity to when the quantity of non-contrast fluid is dispensed. When no hemodynamic pressure signal is present in such instances, the controller may conclude that the quantity of non-contrast fluid was not dispensed into the patient 240 and may refrain from adding the quantity of non-contrast fluid to the dispensed quantity 242. The controller may be configured to add the quantity of dispensed non-contrast fluid to a dispensed quantity if a hemodynamic pressure signal is present in temporal proximity to when the quantity of non-contrast fluid is dispensed. When the hemodynamic pressure signal is present in such instances, the controller may conclude that the quantity of non-contrast fluid was dispensed into the patient 246 and may continue by adding the quantity of non-contrast fluid to the dispensed quantity 248. Thus, by adding or refraining from adding the quantity of dispensed non-contrast fluid to the dispensed quantity based on the presence of the hemodynamic pressure signal, the dispensed quantity may accurately reflect how much non-contrast fluid was actually dispensed into the patient.

The controller may be able to compare the injection quantity to a predetermined threshold to protect against injecting too much non-contrast fluid into a patient. As shown, the controller may determine whether the dispensed quantity exceeds a predetermined threshold 250. In some embodiments, the controller may be configured to notify the user (e.g., via the user interface) if the dispensed quantity exceeds the predetermined threshold. When the dispensed quantity exceeds the predetermined threshold, the controller may provide a notification 252. In some instances, when a notification occurs, the injection procedure may end 254. In some instances, there may be multiple notifications depending on how close the dispensed quantity is getting to a level that might cause harm to a patient. In some embodiments, a user may progressively dispense quantities of non-contrast fluid into the patient's vasculature during an injection procedure and be notified before dispensing undesired quantities of non-contrast fluid into the patient.

As shown, at different points during the injection procedure, the user can determine whether or not to continue the injection procedure 244. To continue the injection procedure, the user may again provide a command to begin dispensing fluid to the controller (212 of FIG. 2A), and the procedure can continue as described. To discontinue the injection procedure, for example, after imaging is complete, the user may end the injection procedure 254 and not dispense any more quantities of non-contrast fluid into the patient. When the injection procedure has ended 234, a final dispensed quantity, corresponding to the total quantity of non-contrast fluid that was actually dispensed into the patient, can be provided to the user and subsequently to the patient's medical record.

In some embodiments, the controller may tabulate the injection quantity and/or the dispensed quantity in real time as fluid is being dispensed from the powered fluid injector. In some embodiments, the controller can determine whether fluid is being delivered into a patient's vasculature or not while the fluid is being dispensed from the powered fluid injector (e.g., based on whether a hemodynamic pressure signal from the invasive blood pressure sensor is present or not just prior to or just after dispensation). In some embodiments, the controller may cause the injection quantity and/or the dispensed quantity to be displayed to the user in real time (e.g., via the user interface). The user may be able to determine whether to continue delivering fluid into the patient's vasculature or not based on the displayed injection quantity and/or dispensed quantity. In some embodiments, the injection quantity and/or the dispensed quantity, as well as the predetermined threshold, may be displayed to the user. In many embodiments, the controller may automatically exclude fluid that is not delivered into the patient from the injection quantity and/or dispensed quantity rather than requiring the user to designate when fluid is not delivered into the patient (e.g., by pressing a purge button on the user interface). In some embodiments, the controller may provide an injection quantity capturing how much contrast fluid has actually been injected into a patient's vasculature and a dispensed quantity capturing how much non-contrast fluid has actually been dispensed into the patient's vasculature. In some such embodiments, the controller can provide running totals of such quantities as fluid is being dispensed from the powered fluid injector.

The injection quantity and/or dispensed quantity may reset when a medical intervention for a patient is complete. In situations in which there are multiple injection procedures in a single medical intervention, the injection quantity and/or the dispensed quantity may reflect all the fluid of each kind that was delivered into the patient's vasculature in all the injection procedures during the medical intervention (e.g., separate total injection and dispensed quantities). In some such instances, the injection quantity and/or the dispensed quantity may be broken down to reflect how much of each kind of fluid was delivered in each of the injection procedures.

Figure 3:
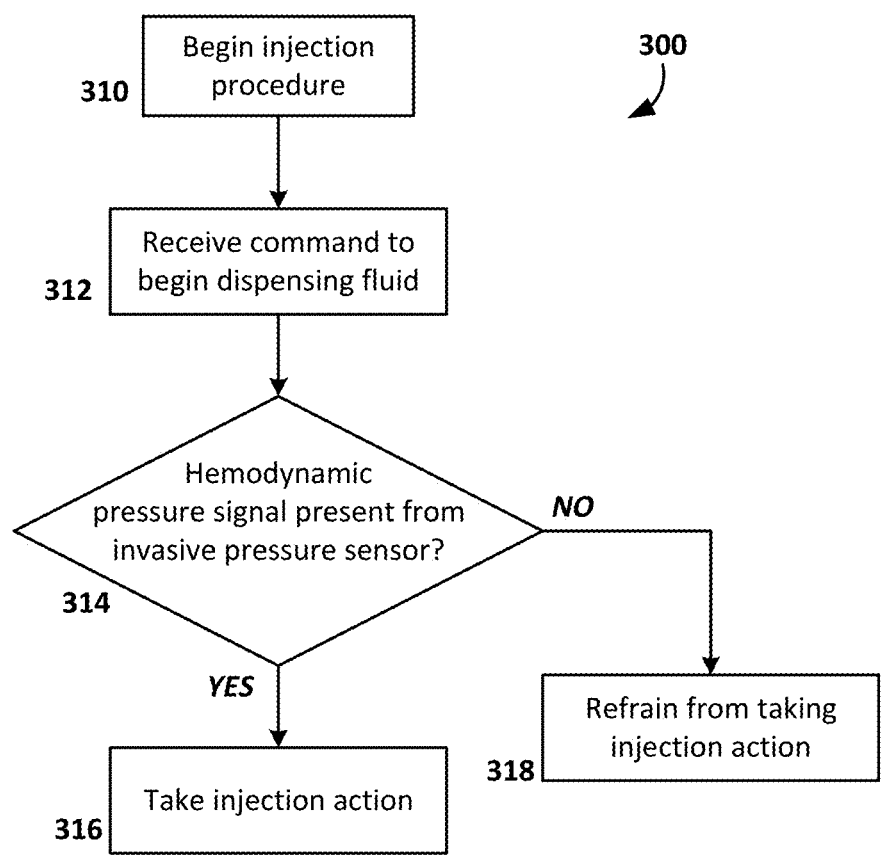
FIG. 3 is a flowchart of an illustrative method for determining whether to take an injection action based on whether a hemodynamic pressure signal is present from an invasive pressure sensor.

Controllers of injection systems discussed herein may cause the systems to perform various functions. FIG. 3 shows a method 300 that the controller may cause the injection system to perform. In some embodiments, the injection procedure begins 310 in a manner similar to those discussed elsewhere herein. The controller may receive a command from a user to begin dispensing fluid (e.g., contrast fluid or non-contrast fluid) 312. The controller may determine whether a hemodynamic pressure signal is present from the invasive blood pressure sensor 314. The controller may assess any pressure signal received from the pressure sensor to determine if it has one or more attributes consistent with those of a valid hemodynamic pressure signal (e.g., a specific amplitude, a specific periodicity, etc.). If the controller determines that the hemodynamic pressure signal is indeed present, the controller may take an injection action 316. In many embodiments, the controller may take the injection action 316 only if a hemodynamic pressure signal is present from the invasive blood pressure sensor. If the controller determines that no hemodynamic pressure signal is present, the controller may refrain from taking an injection action 318.

In different embodiments, the injection action can be an assortment of different actions. For example, in some embodiments, the injection action may include causing the powered fluid injector to dispense a quantity of fluid in response to the command to begin dispensing fluid. In such embodiments, the injection action may include adding the quantity of fluid to a counted quantity if the hemodynamic pressure signal is present in temporal proximity to when the quantity of fluid is dispensed. In some embodiments, the controller may be configured to compare the counted quantity of fluid that has actually been delivered into the patient's vasculature and to notify the user if the injection quantity exceeds a threshold.

As noted elsewhere herein, in some embodiments, the controller may confirm that the catheter is inside the patient's vasculature and in fluidic connection with a pressure transducer that is connected to the powered fluid injector both before and after dispensation of fluid. The controller may be configured to determine whether the hemodynamic pressure signal is present from the invasive blood pressure sensor after the powered fluid injector has dispensed the quantity of fluid. In such embodiments, the injection action may include adding the quantity of dispensed fluid to the counted quantity only if the hemodynamic pressure signal is present both before the quantity of fluid is dispensed and after the quantity of fluid is dispensed.

Some powered fluid injectors include an air bubble detector that is configured to detect air bubbles in tubing that is connectable to the catheter. Delivering such air bubbles to the patient can cause significant adverse consequences. In such instances, the controller may be configured to receive an air bubble signal from the air bubble detector that an air bubble has been detected. In such embodiments, the injection action may include preventing the powered fluid injector from dispensing fluid based on the air bubble. In some embodiments, the controller may be configured to notify the user that he/she is attempting to purge the air bubble while the catheter is inside a patient's vasculature and in fluidic connection with the pressure transducer.

In some instances, the controller may take additional actions after preventing the powered fluid injector from dispensing fluid based on the air bubble. For example, the user may disconnect the patient catheter from the powered fluid injector tubing and enter a second command to purge the air bubble from the powered fluid injector tubing. The controller may receive the second command from the user to begin dispensing fluid. The controller may then determine again whether the hemodynamic pressure signal is present from the invasive blood pressure sensor. The controller may cause the powered fluid injector to dispense a quantity of fluid to purge the air bubble in response to the second command only if the hemodynamic pressure signal is no longer present from the invasive blood pressure sensor.

Figure 4:
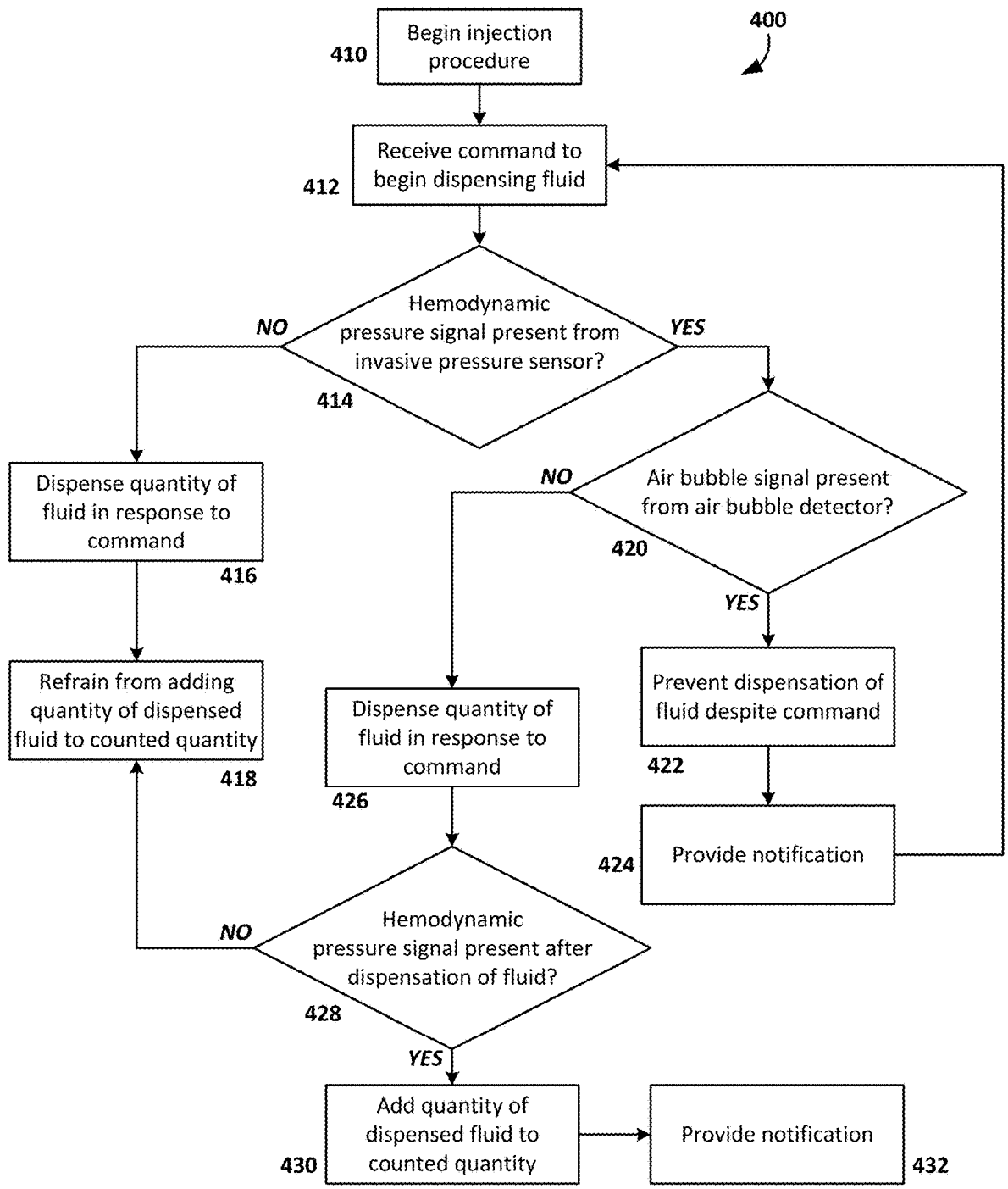
FIG. 4 is a flowchart of an illustrative method of operating a system that includes a powered fluid injector.

As in other methods discussed herein, the method of FIG. 4 starts with beginning an injection procedure 410. The powered injection system's controller may receive a command to begin dispensing fluid 412 (e.g., contrast fluid or non-contrast fluid). Before the powered injection system dispenses the fluid, the controller may determine whether there is a hemodynamic pressure signal present from the invasive pressure sensor 414. The controller may assess any pressure signal received from the pressure sensor to determine if it has one or more attributes consistent with those of a valid hemodynamic pressure signal (e.g., a specific amplitude, a specific periodicity, etc.). If there is no hemodynamic pressure signal, the controller may infer that the patient catheter is not connected to the powered fluid injector's patient tubing and that any fluid dispensed by the powered fluid injector will not be delivered into the patient's vasculature. In such instances, the controller may cause the powered fluid injector to proceed with dispensing the requested fluid 416, but the controller may refrain from adding the dispensed quantity of fluid to the quantity that is counted as being delivered into the patient's vasculature 418 (e.g., an injected quantity of contrast fluid injected into the patient's vasculature or a dispensed quantity of non-contrast fluid dispensed into the patient's vasculature).

If the controller receives the command to begin dispensing fluid 412 and determines that a hemodynamic pressure signal is indeed present from the invasive pressure sensor 414, the controller may make one or more additional determinations before causing the powered fluid injector to dispense fluid in response to the command. For example, the controller may determine whether an air bubble signal is present from an air bubble detector 420. In some instances, the user may take steps to purge one or more air bubbles from somewhere the powered fluid injector, mistakenly thinking that the patient catheter is disconnected from the powered fluid injector. If the user's command to begin dispensing fluid 412 was for purposes of purging an air bubble, the controller may automatically detect such a mistake and prevent the powered fluid injector from dispensing fluid despite the user's command 422. In such instances, the controller may notify the user that he/she is trying to purge an air bubble while the patient catheter is in fluidic connection with the powered fluid injector's tubing and that therefore the powered fluid injector is not permitted to dispense fluid 424. If the controller determines that no air bubble signal is present from the air bubble detector 420, the controller may proceed to cause the powered fluid injector to dispense a quantity of fluid in response to the command from the user 426.

In some embodiments, the controller may once again determine whether a hemodynamic pressure signal is present from the invasive pressure sensor after the powered fluid injector has ceased dispensing fluid 428. The controller may assess any pressure signal received from the pressure sensor to determine if it has one or more attributes consistent with those of a valid hemodynamic pressure signal (e.g., a specific amplitude, a specific periodicity, etc.). If the hemodynamic pressure signal is no longer present, the controller may refrain from adding the quantity of dispensed fluid to the counted quantity 418. If, on the other hand, the hemodynamic pressure signal is still present, the controller may add the quantity of dispensed fluid to the counted quantity 430. In some embodiments, as discussed elsewhere herein, the controller may be configured to compare the counted quantity with a predetermined threshold and to notify the user if the counted quantity exceeds the threshold 432.

Non-transitory computer-readable storage article embodiments can also be used for any of the methods discussed herein (e.g., quantifying how much fluid is delivered into a patient by a powered fluid injector). In various embodiments of such a non-transitory computer-readable storage article, one or more of the details provided above in reference to any of the figures can be implemented in computer-executable instructions stored on the non-transitory computer-readable storage article. It is to be understood that the term "non-transitory," as used herein, is a limitation of the medium itself (e.g., tangible, not a signal) as opposed to a limitation on data storage persistency (e.g., RAM vs. ROM).

Various examples have been described with reference to certain disclosed embodiments. The embodiments are presented for purposes of illustration and not limitation. One skilled in the art will appreciate that various changes, adaptations, and modifications can be made without departing from the scope of the invention.

The invention claimed is:

1. A system comprising:
a powered fluid injector;
a catheter fluidly connectable to the powered fluid injector, the catheter including an invasive blood pressure sensor that is configured to provide a hemodynamic pressure signal only when the catheter is inside a patient's vasculature and in fluidic connection with a pressure transducer that is connected to the powered fluid injector; and
a controller configured to:
receive a command from a user to begin dispensing contrast fluid;
determine whether the hemodynamic pressure signal is present from the invasive blood pressure sensor;
cause the powered fluid injector to dispense a quantity of contrast fluid in response to the command;
add the quantity of contrast fluid to an injection quantity if the hemodynamic pressure signal is present in temporal proximity to when the quantity of contrast fluid is dispensed; and
refrain from adding the quantity of contrast fluid to the injection quantity if the hemodynamic pressure signal is not present in temporal proximity to when the quantity of contrast fluid is dispensed.

2. The system of claim 1, wherein the controller is configured to determine whether the hemodynamic pressure signal is present by determining whether the hemodynamic pressure signal is present within a predetermined amount of time before the controller causes the powered fluid injector to begin dispensing the quantity of contrast fluid.

3. The system of claim 2, wherein the controller is configured to determine whether the hemodynamic pressure signal is present by further determining whether the hemodynamic pressure signal is present within a predetermined amount of time of the controller causing the powered fluid injector to cease dispensing the quantity of contrast fluid.

4. The system of claim 1, wherein the controller is configured to determine whether the hemodynamic pressure signal is present by determining whether the hemodynamic pressure signal is present within a predetermined amount of time of the controller causing the powered fluid injector to cease dispensing the quantity of contrast fluid.

5. The system of claim 1, wherein the catheter comprises a guide catheter.

6. The system of claim 1, wherein the catheter comprises a diagnostic catheter.

7. The system of claim 1, wherein the controller is further configured to notify the user if the injection quantity exceeds a threshold.

8. The system of claim 1, wherein the controller is further configured to:
receive a second command from the user to begin dispensing non-contrast fluid;
cause the powered fluid injector to dispense a quantity of non-contrast fluid in response to the second command;
add the quantity of non-contrast fluid to a dispensed quantity if the hemodynamic pressure signal is present in temporal proximity to when the quantity of non-contrast fluid is dispensed; and
refrain from adding the quantity of non-contrast fluid to the dispensed quantity if the hemodynamic pressure signal is not present in temporal proximity to when the quantity of non-contrast fluid is dispensed.

9. The system of claim 1, wherein the controller is configured to determine whether the hemodynamic pressure signal is present by assessing a pressure signal from the invasive blood pressure sensor to determine whether the pressure signal from the invasive blood pressure sensor constitutes a valid hemodynamic pressure signal.

10. The system of claim 9, wherein assessing the pressure signal from the invasive blood pressure sensor comprises assessing an amplitude and/or a periodicity of the pressure signal from the invasive blood pressure sensor.

\* \* \* \* \*